United States Patent
Wadle et al.

(10) Patent No.: US 6,221,370 B1
(45) Date of Patent: Apr. 24, 2001

(54) FATTY ACID ETHOXYLATES AND PARTIAL GLYCERIDES FOR PREPARING PHASE INVERSION TEMPERATURE EMULSIONS

(75) Inventors: Armin Wadle, Cerny (FR); Achim Ansmann, Erkrath (DE); Holger Tesmann, Juechen (DE); Karl-Heinz Gantke, Moenchengladbach (DE); Ansgar Behler, Bottrop (DE); Bernhard Guckenbiehl, Duesseldorf (DE)

(73) Assignee: Henkel Kommanditgesellschaft auf Aktien, Duesseldorf (DE)

( * ) Notice: Subject to any disclaimer, the term of this patent is extended or adjusted under 35 U.S.C. 154(b) by 0 days.

(21) Appl. No.: 09/254,029

(22) PCT Filed: Aug. 25, 1997

(86) PCT No.: PCT/EP97/04621

§ 371 Date: Feb. 26, 1999

§ 102(e) Date: Feb. 26, 1999

(87) PCT Pub. No.: WO98/09721

PCT Pub. Date: Mar. 12, 1998

(30) Foreign Application Priority Data

Sep. 2, 1996 (DE) ............................................. 196 35 553

(51) Int. Cl.$^7$ .................................................. A61K 9/107
(52) U.S. Cl. ..................... 424/401; 424/70.1; 424/78.03; 514/937; 514/975
(58) Field of Search .................................. 424/401, 70.1, 424/78.03; 514/937, 975

(56) References Cited

U.S. PATENT DOCUMENTS

| | | |
|---|---|---|
| 3,547,828 | 12/1970 | Mansfield . |
| 3,707,535 | 12/1972 | Lew . |
| 3,772,269 | 11/1973 | Lew . |
| 3,839,318 | 10/1974 | Mansfield . |
| 4,172,887 | 10/1979 | Vanlerberghe et al. . |
| 4,349,669 | 9/1982 | Klahr et al. . |

FOREIGN PATENT DOCUMENTS

| | | |
|---|---|---|
| 1 344 458 | 2/1995 | (CA) . |
| 40 10 393 | 10/1991 | (DE) . |
| 0 077 167 | 4/1983 | (EP) . |
| 0 345 586 | 12/1989 | (EP) . |
| 0 617 955 | 10/1994 | (EP) . |
| 962 919 | 7/1964 | (GB) . |
| 2 278 780 | 12/1994 | (GB) . |
| 93/11865 | 6/1993 | (WO) . |

OTHER PUBLICATIONS

Derwent Patent Abstract (WPAT) 89–364978/50.
Derwent Patent Abstract (WPAT) 93–197783/25.
Derwent Patent Abstract (WPAT) 91–296733/41.
Derwent Patent Abstract (WPAT) 95–014884/03.
Derwent Patent Abstract (WPAT) 95–171245/23.
Derwent Patent Abstract (WPAT) 95–352054/46.
Derwent Patent Abstract (WPAT) 66–10585F/00.
Derwent Patent Abstract (WPAT) 71–10582S/06.
Derwent Patent Abstract (WPAT) 81/53579D/30.
Derwent Patent Abstract (WPAT) 75–39724W/24.
Derwent Patent Abstract (WPAT) 70–14249R/09.

*Primary Examiner*—Raj Bawa
(74) *Attorney, Agent, or Firm*—John E. Drach; Glenn E. J. Murphy; Henry E. Millson, Jr.

(57) ABSTRACT

An emulsifier mixture for use in the production of phase inversion temperature (PIT) emulsions is provided. The emulsifier mixture comprises fatty acid ethoxylates and partial glycerides which enable PIT emulsions to be produced at a given phase inversion temperature irrespective of the polarity of the oils, allowing for the emulsifying of a broad range of oils irrespective of their character, under the same conditions.

17 Claims, No Drawings

FATTY ACID ETHOXYLATES AND PARTIAL GLYCERIDES FOR PREPARING PHASE INVERSION TEMPERATURE EMULSIONS

BACKGROUND OF THE INVENTION

1. Field of the Invention

This invention relates to new emulsifier mixtures based on selected-nonionic surfactants and to their use for the production of PIT emulsions.

2. Discussion of Related Art

Mixtures of hydrophilic emulsifiers and hydrophobic co-emulsifiers are normally used for the production of fine-droplet emulsions by the phase inversion temperature (PIT) method (cf. DE-A1 38 19 193, DE-A1 40 10 393, DE-A1 4 140 562, DE-A1 43 18 171, DE-A1 43 37 041, DE-A1 44 11 557 [Henkel]). According to the prior art, the proportions of emulsifier and co-emulsifier have to be adapted to the oil character (expressed through the so-called ACN number) for PIT emulsion technology. Accordingly, there are no known emulsifier/co-emulsifier mixtures which would be capable of emulsifying various oils under the same temperature conditions by the PFT method. It is obvious that such mixtures would make the production of stable emulsions much easier. Accordingly, the problem addressed by the present invention was to provide emulsifier mixtures without any of the disadvantages mentioned above for the production of PIT emulsions.

Other than in the operating examples, or where otherwise indicated, all numbers expressing quantities of ingredients or reaction conditions used herein are to be understood as modified in all instances by the term "about."

3. Description of the Invention

The present invention relates to emulsifier mixtures containing (a) fatty acid ethoxylates and
(b) partial glycerides.

It has surprisingly been found that the mixtures according to the invention enable PIT emulsions to be produced at a given phase inversion temperature irrespective of the ACN number, i.e. the polarity of the oils. Accordingly, the mixtures are suitable for emulsifying a broad range of oils, irrespective of their character, under the same conditions.

Fatty acid ethoxylates

Fatty acid ethoxylates suitable as emulsifier component (a) preferably correspond to formula (I):

$$R^1CO(CH_2CH_2O)_nH \quad (I)$$

in which $R^1CO$ is a linear or branched acyl group containing 12 to 22 carbon atoms and n is a number of 5 to 50 and preferably 15 to 35. Typical examples are products of the addition of 20 to 30 moles of ethylene oxide with lauric acid, isotridecanoic acid, myristic acid, palmitic acid, palmitoleic acid, stearic acid, isostearic acid, oleic acid, elaidic acid, petroselic acid, linoleic acid, linolenic acid, elaeostearic acid, arachic acid, gadoleic acid, behenic acid and erucic acid and the technical mixtures thereof obtained, for example, in the pressure hydrolysis of natural fats and oils or in the reduction of aldehydes from Roelen's oxo synthesis. Adducts of 20 to 30 moles of ethylene oxide with fatty acids containing 16 to 18 carbon atoms are preferably used.

Partial glycerides

Partial glycerides suitable as emulsifier component (b) preferably correspond to formula (II):

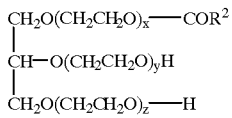

in which $R^2CO$ is a linear or branched acyl group containing 12 to 22 carbon atoms and x, y and z together stand for 0 or for numbers of 1 to 50 and preferably 15 to 35. Typical examples of partial glycerides suitable for the purposes of the invention are lauric acid monoglyceride, cocofatty acid monoglyceride, palmitic acid monoglyceride, stearic acid monoglyceride, isostearic acid monoglyceride, oleic acid monoglyceride and tallow fatty acid monoglyceride and adducts thereof with 5 to 50 and preferably 20 to 30 moles of ethylene oxide. Monoglycerides or technical monoglyceride-dominated mono/diglyceride mixtures corresponding to formula (II) in which $R^2CO$ is a linear acyl group containing 16 to 18 carbon atoms are preferably used.

Emulsifier mixtures containing components (a) and (b) in a ratio by weight of 10:90 to 90:10, preferably 25:75 to 75:25 and more preferably 40:60 to 60:40 are normally used.

Commercial applications

Stable PIT emulsions containing oils of various polarities can be produced with the emulsifier mixtures. Accordingly, the present invention also relates to the use of the emulsifier mixtures for the production of PIT emulsions, the mixtures generally being used in quantities of 1 to 10% by weight and preferably 3 to 8% by weight, based on the emulsions.

Oils

Suitable oils are, for example. Guerbet alcohols based on fatty alcohols containing 6 to 18 and preferably 8 to 10 carbon atoms, esters of linear $C_{6-20}$ fatty acids with linear $C_{6-20}$ fatty alcohols, esters of branched $C_{6-13}$ carboxylic acids with linear $C_{6-20}$ fatty alcohols, esters of linear $C_{6-18}$ fatty acids with branched alcohols, more particularly 2-ethyl hexanol, esters of linear and/or branched fatty acids with polyhydric alcohols (for example dimer diol or trimer triol) and/or Guerbet alcohols, triglycerides based on $C_{6-10}$ fatty acids, vegetable oils, branched primary alcohols, substituted cyclohexanes. Guerbet carbonates, dialkyl ethers and/or aliphatic or naphthenic hydrocarbons which are used in quantities of normally 10 to 50% by weight and preferably 15 to 35% by weight.

The PIT emulsions may be used for a number of applications, but are preferably used for the production of skin-care and hair-care products such as for example, hair shampoos, hair lotions, foam baths, cremes, lotions or emollients. They may also contain surfactants, co-emulsifiers, superfatting agents, stabilizers, waxes, consistency regulators, thickeners, cationic polymers, silicone compounds, biogenic agents, antidandruff agents, film formers, preservatives, hydrotropes, solubilizers, UV absorbers, dyes and fragrances and the like as further auxiliaries and additives.

Typical examples of suitable surfactants are fatty alcohol polyglycol ether sulfates, monoglyceride sulfates, mono- and/or dialkylsulfosuccinates, fatty acid isethionates, fatty acid sarcosinates, fatty acid taurides, ether carboxylic acids, alkyl oligoglucosides, fatty acid glucamides, alkyl amidobetaines and/or preferably vegetable protein fatty acid condensates.

Suitable co-emulsifiers are, for example, nonionic surfactants from at least one of the following groups:

(b1) products of the addition of 2 to 30 moles of ethylene oxide and/or 0 to 5 moles of propylene oxide onto linear fatty alcohols-containing 8 to 22 carbon atoms and onto alkylphenols containing 8 to 15 carbon atoms in the alkyl group;

(b2) glycerol monoesters and diesters and sorbitan monoesters and diesters of saturated and unsaturated fatty acids containing 6 to 22 carbon atoms and ethylene oxide adducts thereof;

(b3) alkyl mono- and oligoglycosides containing 8 to 22 carbon atoms in the alkyl group and ethoxylated analogs thereof;

(b4) adducts of 15 to 60 moles of ethylene oxide with castor, oil and/or hydrogenated caster oil;

(b5) polyol esters and, in particular, polyglycerol esters such as, for example, polyglycerol polyricinoleate or polyglycerol poly-12-hydroxystearate. Mixtures of compounds from several of these classes are also suitable;

(b6) products of the addition of 2 to 15 moles of ethylene oxide onto castor oil and/or hydrogenated castor oil;

(b7) partial esters based on linear, branched, unsaturated or saturated $C_{12/22}$ fatty acids, ricinoleic acid and 12-hydroxystearic acid and glycerol, polyglycerol, pentaerythritol, dipentaerythritol, sugar alcohols (for example sorbitol) and polyglucosides (for example cellulose);

(b8) trialkyl phosphates;

(b9) wool wax alcohols;

(b10) polysiloxane/polyalkyl polyether copolymers and corresponding derivatives;

(b11) mixed esters of pentaerythritol, fatty acids, citric acid and fatty alcohol according to DE-PS 11 65 574 and (b12) polyalkylene glycols.

The addition products of ethylene oxide and/or propylene oxide with fatty alcohols, alkylphenols, glycerol monoesters and diesters and sorbitan monoestes and diesters of fatty acids or with castor oil are known, commercially available products. They are homolog mixtures of which the average degree of alkoxylation corresponds to the ratio between the quantities of ethylene oxide and/or propylene oxide and substrate with which the addition reaction is carried out.

$C_{8/18}$ alkyl mono- and oligoglycosides, their production and their use as surfactants are known, for example, from U.S. Pat. No. 3,839,318, U.S. Pat. No. 3,707,535, U.S. Pat. No. 3,547,828, DE-OS 19 43 689, DE-OS 20 36 472 and DE-A1 30 01 064 and EP-A 0 077 167. They are produced in particular by reacting glucose or oligosaccharides with primary $C_{8/18}$ alcohols. So far as the glycoside unit is concerned, both monoglycosides in which a cyclic sugar unit is attached to the fatty alcohol by a glycoside bond and oligomeric glycosides with a degree of oligomerization of preferably up to about 8 are suitable. The degree of oligomerization is a statistical mean value on which the homolog distribution typical of such technical products is based.

Zwitterionic surfactants may also be used as emulsifiers. Zwitterionic surfactants are surface-active compounds which contain at least one quaternary ammonium group and at least one carboxylate and one sulfonate group in the molecule. Particularly suitable zwitterionic surfactants are the so-called betaines, such as the N-alkyl-N,N-dimethyl ammonium-glycinates, for example cocoalkyl dimethyl ammonium glycinate, N-acylaminopropyl-N,N-dimethyl ammonium glycinates, for example cocoacylaminopropyl dimethyl ammonium glycinate, and 2-alkyl-3-carboxylmethyl-3-hydroxyethyl imidazolines containing 8 to 18 carbon atoms in the alkyl or acyl group and cocacylaminoethyl hydroxyethyl carboxymethyl glycinate. The fatty acid amide derivatives known under the CTFA name of Cocamidopropyl Betaine is particularly preferred. Ampholytic surfactants are also suitable emulsifiers. Ampholytic surfactants are surface-active compounds which, in addition to a $C_{8/18}$ alkyl or acyl group, contain at least one free amino group and at least one —COOH— or —SO$_3$H— group in the molecule and which are capable of forming inner salts. Examples of suitable ampholytic surfactants are N-alkyl glycines, N-alkyl propionic acids, N-alkylaminobutyric acids. N-alkyliminodipropionic acids, N-hydroxyethyl-N-alkylamidopropyl glycines, N-alkyl taurines, N-alkyl sarcosines, 2-alkylaminopropionic acids and alkylaminoacetic acids containing around 8 to 18 carbon atoms in the alkyl group. Particularly preferred ampholytic surfactants are N-cocoalkylaminopropionate, cocoacylaminoethyl aminopropionate and $C_{12/18}$ acyl sarcosine. Besides the ampholytic emulsifiers, quaternary emulsifiers may also be used, those of the esterquat type, preferably methyl-quanternized difatty acid triethanolamine ester salts, being particularly preferred.

The superfatting agents used may be such substances as, for example, lanolin and lecithin and polyethoxylated or acylated lanolin and lecithin derivatives, polyol fatty acid esters and fatty acid alkanolamides, the latter also serving as foam stabilizers. Suitable consistency regulators are above all, fatty alcohols containing 12 to 22 and preferably 16 to 18 carbon atoms. These substances are preferably used in combination with alkyl oligoglucosides and/or fatty acid-N-methyl glucamides of the same chain length and/or polyglycerol poly-12-hydroxystearates. Suitable thickeners are, for example, polysaccharides, more particularly xanthan gum, guar guar, agar agar, alginates and tyloses, carboxymethyl cellulose and hydroxyethyl cellulose, relatively high molecular weight polyethylene glycol monoesters and diesters of fatty acids, polyacrylates, polyvinyl alcohol and polyvinyl pyrrolidone, surfactants such as, for example, ethoxylated fatty acid glycerides, esters of fatty acids with polyols such as, for example, pentaerythritol or trimethylol propane, narrow-range fatty alcohol ethoxylates or alkyl oligoglucosides and electrolytes, such as sodium chloride and ammonium chloride.

Suitable cationic polymers are, for example, cationic cellulose derivatives, cationic starch, copolymers of diallyl ammonium salts and acrylamides, quaternized vinyl pyrrolidone/vinyl imidazole polymers such as, for example, Luviquat® (BASF AG, Ludwigshafen, FRG), condensation products of polyglycols and amines, quaternized collagen polypeptides such as, for example, Lauryldimonium Hydroxypropyl Hydrolyzed Collagen (Lamequat®L/Grüau GmbH), quaternized wheat polypeptides, polyethyleneimine, cationic silicone polymers such as, for example, Amidomethicone or Dow Corning (Dow Corning Co., USA), copolymers of adipic acid and dimethyl amino-hydroxypropyl diethylenetriamine (Cartaretine®, Sandow/CH), polyaminopolyamides as described, for example, in FR-A 2252840 and crosslinked water-soluble polymers thereof, cationic chitin derivatives such as, for example, quaternized chitosan, optionally in microcrystalline distribution, condensation products of dihaloalkyls such as, for example, dibromobutane with bis-dialkylamines such as, for example, bis-dimethylamino-1,3-propane, cationic guar gum such as, for example, Jaquar° CBS, Jaguar® C-17, Jaguar® C-16 of Celanese/USA, quaternized ammonium salt polymers such as, for example, Mirapol® A-15, Mirapol® AD-1, Mirapol® AZ-1 of Miranol/USA.

Suitable silicone compounds are, for example, dimethyl polysiloxanes, methyl phenyl polysiloxanes, cyclic silicones and amino-, fatty acid, alcohol-, polyether-, epoxy, fluorine- and/or alkyl-modified silicone compounds which may be both liquid and resin-like at room temperature. Typical examples of fats are glycerides while suitable waxes are inter alia beeswax, paraffin wax or microwaxes, optionally in combination with hydrophilic waxes, for example cetostearyl alcohol. The pearlescing waxes used may be, in particularly, mono- and difatty acid esters of polyalkylene glycols, partial glycerides or esters of fatty alcohols with polybasic carboxylic acids or hydroxycarboxylic acids. Suitable stabilizers are metal salts of fatty acids such as, for example, magnesium, aluminum and/or zinc stearate. Biogenic agents in the context of the invention are, for example, bisabolol, allantoin, phytantriol, panthenol, AHA acids, plant extracts and vitamin complexes. Suitable antidandruf agents are climbazol, octopirex and zinc pyrethion. Typical film formers are, for example, chitosan, microcrystalline chitosan, quanterized chitosan, polyvinyl, pyrrolidone, vinyl pyrrolidone/vinyl acetate copolymers, polymers of the acrylic acid series, quaternary cellulose derivatives, collagen, hyaluronic acid and salts thereof and similar compounds. In addition, hydrotropes such as, for example, ethanol, isopropyl alcohol, propylene glycol or glucose may be used to improve flow behavior. Suitable preservatives are, for example, phenoxyethanol, formaldehyde solution, parabens, pentanefiol or sorbic acid. Suitable dyes are any of the substances suitable and approved for cosmetic purposes as listed, for example in the publication "Kosmetische F ärbemittel" of the Farbstoffkommission der Deutschen Forschungsgemeinschaft, Verlag Chemie, Weinheim, 1984, pages 81 to 106. These dyes are normally used in concentrations of 0.001 to 0.1% by weight, based on the mixture as a whole.

The total percentage content of auxiliaries and additives may be from 1 to 50% by weight and is preferably from 5 to 40% by weight, based on the particular formulation.

EXAMPLES

Emulsions based on oils differing in polarity were prepared by the PIT method using emulsifier mixtures according to the invention (F1 to F3) and a comparison mixture (F4). The emulsions were stored to 4 weeks at 40° C. and then visually examined for stability. The results are set out in Table 1

TABLE 1

Stability of emulsions (quantities in % by weight)

| | F1 | F2 | F3 | F4 |
|---|---|---|---|---|
| Palmitic/stearic acid + 30 EO | 3.3 | 3.3 | 1.7 | — |
| Cetearyl alcohol + 30 EO | — | — | — | 3.3 |
| Glyceryl stearate | 3.3 | 3.3 | 1.7 | 3.3 |
| Cetiol LC | 20.0 | — | — | — |
| Oleyl Oleate | — | 20.0 | — | 20.0 |
| Capric/Caprylic Triglycerides | — | — | 5.0 | — |
| Paraffin oil, low-viscosity | — | — | 5.0 | — |
| Water | to 100 | | | |
| PIT [° C.] | 85 | 85 | 85 | — |
| Stability after 3 weeks' storage at 40° C. | Stable | Stable | Stable | Stable |

It can be seen that, if the fatty acid ethoxylates are replaced by fatty alcohol ethoxylates, the PIT emulsions obtained are not stable.

What is claimed is:

1. A method for the production of a phase inversion temperature (PIT) emulsion comprising:
   (a) forming a stable emulsifier mixture comprising:
   (1) at least one fatty acid ethoxylate corresponding to the formula $$R^1CO(CH_2CH_2O)_nH \quad (I)$$

wherein $R^1CO$ is a linear or branched acyl group having from 12 to 22 carbon atoms and n is a number of from 5 to 50; and
   (2) at least one partial glyceride corresponding to the formula

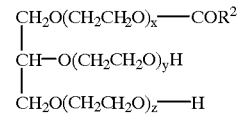

wherein $R^2CO$ is a linear or branched acyl group having from 12 to 22 carbon atoms and the sum of x, y, and z is a number of from 0 to 50;
   (b) mixing at weight percentages based on the emulsion:
   (1) 1 to 10% of said stable emulsifier mixture;
   (2) 10 to 50% of at least one oil selected from the group consisting of Guerbet alcohols based on fatty alcohols having from 6 to 18 carbon atoms, esters of linear $C_{6-20}$ fatty acids with linear $C_{6-20}$ fatty alcohols, esters of branched $C_{6-13}$ carboxylic acids with linear $C_{6-20}$ fatty alcohols, esters of linear $C_{8-18}$ fatty acids with branched alcohols, esters of linear and/or branched fatty acids with polyhydric alcohols and/or Guerbet alcohols, triglycerides based on $C_{6-10}$ fatty acids, vegetable oils, branched primary alcohols, substituted cyclohexanes, Guerbet carbonates, dialkyl ethers and/or aliphatic or naphthenic hydrocarbons;
   (3) 1 to 50% auxiliaries and additives; and
   (4) water to form a PIT emulsion.

2. The method of claim 1 wherein in the at least one fatty acid ethoxylate corresponding to formula (I), n is a number of from 15 to 35.

3. The method of claim 2 wherein n is a number of from 20 to 30.

4. The method of claim 1 wherein $R^1CO$ has from 16 to 18 carbon atoms.

5. The method of claim 1 wherein in the at least one partial glyceride corresponding to formula (II), the sum of x, y, and z is a number from 15 to 35.

6. The method of claim 1 wherein said at least one partial glyceride is a monoglyceride or technical monoglyceride-dominated mono/diglyceride mixture.

7. The method of claim 1 wherein the at least one partial glyceride has from 5 to 50 moles of ethylene oxide.

8. The method of claim 7 wherein the at least one partial glyceride has from 20 to 30 moles of ethylene oxide.

9. The method of claim 6 wherein $R^2CO$ has from 16 to 18 carbon atoms.

10. The method of claim 1 wherein the ratio of the at lest one fatty acid ethoxylate to the at least one partial glyceride (2) is from 10:90 to 90:10 by weight.

11. The method of claim 10 wherein said ratio of (1) to (2) is from 25:75 to 75:25 by weight.

12. The method of claim 11 wherein said ratio of (1) to (2) is from 50:60 to 60:40 by weight.

13. The method of claim 1 wherein the emulsifier mixture is present in from 3 to 8% by weight based on the emulsion.

14. The method of claim 13 wherein the at least one oil is present in from 15 to 35% by eight based on the emulsion.

15. The method of claim 1 wherein the auxiliaries and additives consist of at least one member selected from the group consisting of surfactants, co-emulsifiers, superfatting agents, stabilizers, waxes, consistency regulators, thickeners, cationic polymers, silicone compounds, biogenic agents, antidandruff agents, film formers, preservatives, hydrotropes, solubilizes, UV absorbers, dyes and fragrances.

16. A stable emulsifier mixture for use in the production of phase inversion temperature (PIT) emulsions comprising:

(a) at least one fatty acid ethoxylate corresponding to the formula $$R^3CO(CH_2CH_2O)_nH \qquad (I)$$

wherein $R^3CO$ is a linear or branched acyl group having from 12 to 22 carbon atoms and n is a number of from 5 to 50; and (b) at least one partial glyceride corresponding to the formula

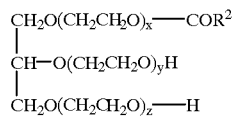

wherein $R^2CO$ is a linear or branched acyl group having from 12 to 22 carbon atoms and the sum of x, y, and z is a number of from 0 to 50.

17. A phase inversion temperature emulsion produced by the method of claim 1.

* * * * *